United States Patent [19]

Van Ackeren et al.

[11] 4,197,013

[45] Apr. 8, 1980

[54] CALIBRATION OF DUST MONITORING INSTRUMENTS

[75] Inventors: Paul Van Ackeren; Heinz Dahlmann; Helmut Gauter; Wilhelm Thielmann, all of Duisburg, Fed. Rep. of Germany

[73] Assignee: Mannesmann Aktiengesellschaft, Dusseldorf, Fed. Rep. of Germany

[21] Appl. No.: 759,484

[22] Filed: Jan. 14, 1977

[30] Foreign Application Priority Data

Jan. 16, 1976 [DE] Fed. Rep. of Germany ....... 2601985

[51] Int. Cl.² ............................................ G01N 21/28
[52] U.S. Cl. .................................... 356/438; 250/252; 250/573
[58] Field of Search ............... 250/252, 573, 574, 564; 356/436–440, 442

[56] References Cited

U.S. PATENT DOCUMENTS

| | | | |
|---|---|---|---|
| 2,244,507 | 6/1941 | Thomas | 250/564 |
| 3,885,162 | 5/1975 | Geertz | 250/573 |
| 4,126,396 | 11/1978 | Hartmann et al. | 250/573 X |

Primary Examiner—John K. Corbin
Assistant Examiner—Bruce Y. Arnold
Attorney, Agent, or Firm—Smyth, Pavitt, Siegemund, Jones & Martella

[57] ABSTRACT

Disclosed is a method and apparatus for calibrating and recalibrating a photometric measurement instrument which supervises the presence of dust in a particular location as produced by a process during which dust is developed on an irregular basis. The method is characterized in that the calibration is initiated upon the detection of a condition in which dust concentration is expected to be low. In a steel-making process, such a condition occurs upon termination of the blowing phase of a converter. In the case of smoke in a flue, such a condition occurs when there is an absence of gas flow in the flue.

6 Claims, 2 Drawing Figures

CALIBRATION OF DUST MONITORING INSTRUMENTS

BACKGROUND OF THE INVENTION

The present invention relates to photometrically monitoring and supervising the emission of dust, and more particulary, the invention relates to calibration of such a photometric process.

The production of dust in processes which are prone to produce dust is usually monitored, possibly quite extensively. For example, blower converters produce a smoke filled gas blast which is wet dedusted or scrubbed before discharge into the outer atmosphere and the discharge flow is monitored as to the dust content. The instrument undertaking the supervision must be frequently recalibrated. For this, automatic calibration equipment is activated intermittently in regular intervals, e.g. in one hour intervals the monitoring equipment is disabled to undergo calibration for about a minute.

During the calibration period measuring data are not available. It was found that this temporary deactivation of the dust monitoring equipment is not acceptable as quite frequently valuable data are lost.

DESCRIPTION OF THE INVENTION

It is an object of the present invention to provide for recalibration of dust supervising and monitoring equipment in such a manner that the supervising and monitoring procedure is minimally interfered with.

In accordance with the preferred embodiment of the invention, it is suggested to separately monitor the dust producing process as to at least one parameter which is indicative of a phase of little or no known dust emission, and to provide for recalibration during such a phase.

By way of example, supervision of the dust producing process may include an instrument with a movable arm (printer, plotter head, etc.). When the arm has a particular deflected position which is indicative that the dust content has dropped below a minimum, an automatic calibration may be instituted. A different approach can be taken, for example, in the particular field of steel making. A blowing converter is a formidable source of smoke and dust, and the blast of gas is usually forced through a wet deduster before the residual gas is permitted to be discharged into the atmosphere. The dust content of the discharge is to be monitored. In accordance with the invention, the calibration of the dust monitor is timed to be dependent upon termination of a blowing phase. In one example, the flow conditions in a discharge flue are monitored and when the flow drops below a given value, a calibration phase is conducted, since little dust is developed while the converter is in operational phases other than blowing.

The calibration procedure instituted should include the establishing of at least two particular signal or output levels, such as a null or zero point and a level well in the range of expected measuring levels.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows a smoke and gas flue 1 connected to a wet deduster of a blowing converter. The flue contains a blower or fan, 3, which is driven by a motor 2 for sucking smoke and gases out of the deduster.

Figure 1:
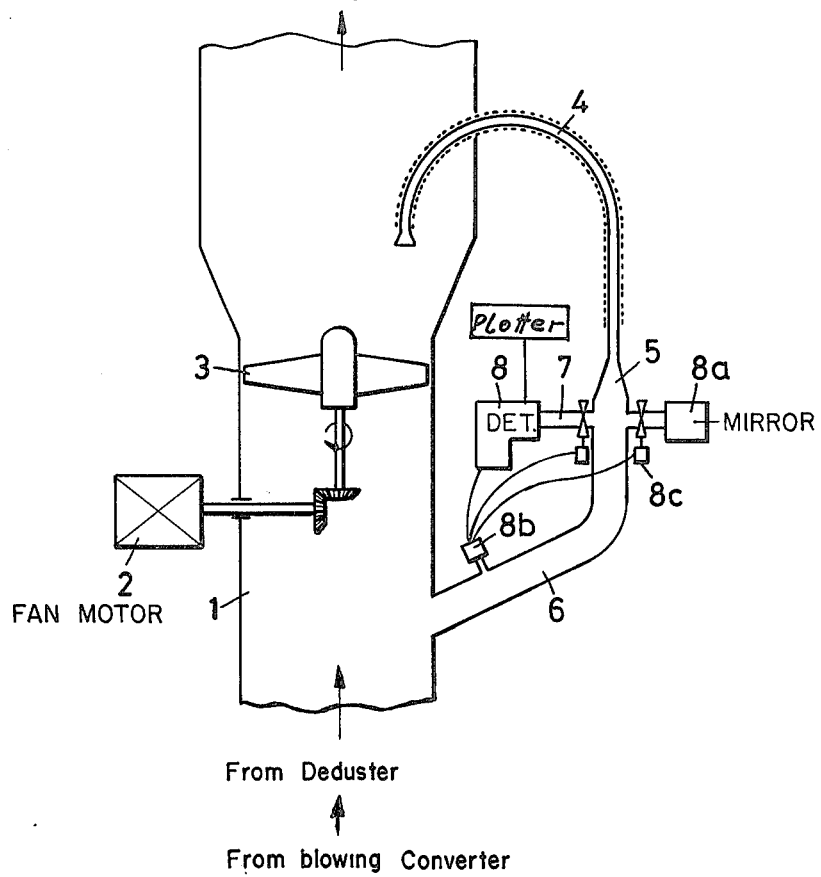
FIG. 1 illustrates an exhaust pipe for wet smoke, fumes and gas, and a photometric dust measuring device improved in accordance with the present invention.

A pickup and sampling tube 4 has its inlet disposed to pick a representative sample of the flue content and flow. The tube 4 is enveloped by a heating spiral. Its other end widens to a measuring chamber 5. Reference numeral 6 denotes a suction pipe leading back to the flue 1 upstream from the blower and pickup to complete the circulation and to obtain suction by means of the passing flow of smoke and gas if there is such a flow.

Figure 2:
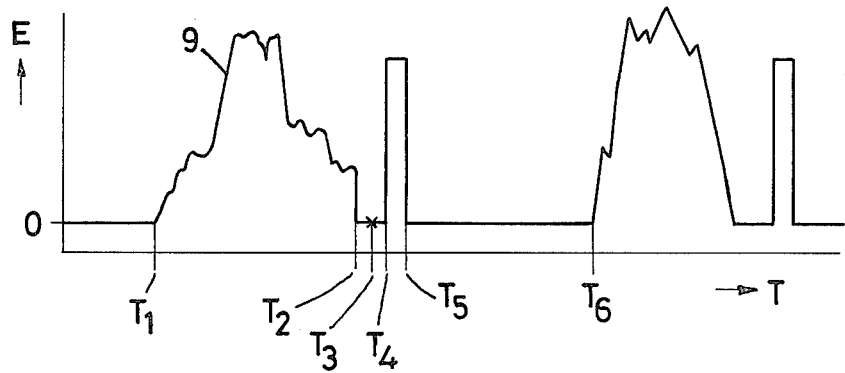
FIG. 2 is a graph showing absorbance as measured by the instrument and plotted vs. time.

Reference numeral 7 refers to a duct which establishes an optical path traversing chamber 5. A light source and photoelectric pickup 8 is disposed at one end of that optical path, while a reflector 8a is disposed at the other end thereof, so that the probing light beam traverses chamber 5 twice. The photometer 8 drives a plotter which produces graphs such as shown in FIG. 2. Particularly, the instrument provides indication and representation of the absorbance, i.e., of the light attenuation coefficient as it is effective in chamber 5 due to its content.

The optical path can be blocked physically as well as optically by two solenoid operated, high speed shutters 8c. The shutters are operated by a pressure sensitive switch 8b which monitors the pressure in duct 6. Generally speaking, the operation may be such that in the absence of a flow in flue 1 switch 8b causes the shutters 8c to close and they are opened only when flow of gas in flue 1 is detected by the switch 8b.

The switch 8b controls, in addition, the photometer 8 to render its operation responsive to absence and presence of a gas and smoke flow in flue 1. This then establishes the responsiveness of the smoke detector to dust producing conditions. Particularly, the presence of flow in flue 1 causes switch 8b to activate photometer 8 to run in the dust monitoring mode, driving the plotter accordingly. In the absence of flow calibration may occur. Calibration proper may be timed to occur shortly after a transition from presence to absence of flow in flue 1.

When the converter is not blowing the motor 2 is off, and pressure sensitive switch 8b will be in a first switching state indicative of absence of flow. This, in turn, indicates that monitoring of dust is not needed or at least is not critical and thus also is indicative of an opportunity to null the instrument. Establishing of the zero point can be carried out in the following manner.

This first switching state of 8b places a mirror and a filter in the optical path from the photometer. The mirror replaces reflector 8a for the calibration. The shutters 8c are closed to protect the instrumentation during this off phase, so that an internal reflector is needed in the instrument. The filter compensates the path differences due to the shorter length of the light path. The need for such a filter depends on the resolution and needed accuracy of the monitor.

An alternative mode of operation is to generate a quasi-zero point by opening, for example, temporarily shutters 8c in which case "background" dust establishes the zero level. The system could, however, be provided with a fresh air feeder path and equipment for chamber 5, purging it from residual dust. In either case a zero line may now be plotted in the output device of photometer 8 to obtain a leader or base line (see FIG. 2).

At some point in time, just prior to $T_1$ the converter will blow and motor 2 will be turned on. This then establishes dust producing conditions. These conditions are sensed by switch 8b as the pressure condition in the duct system changes, and switch 8b responds at time $T_1$ to shift to the second switching state. Shutters 8c open and photometer 8 is rendered operative. Soon the dust content increases and the plotter writes trace 9. The smoke and gas drawn into the measuring system by sampling tube 4 is heated therein above the dew point so that chamber 5 does indeed hold a representative sample of the dust content in flue 1.

The blowing of the converter is terminated prior to $T_2$ but dust development may continue for a little while until at $T_2$ motor 2 is stopped or slowed down. The pressure changes in switch 8b, and the measuring is actually stopped. As far as the system as a whole is concerned, a period of relatively low dust development has begun.

Switch 8b closes again shutters 8c, and deactivates the instrument 8 as to dust monitoring. The instrument 8 now contains a timer circuit which is triggered by the transition of the switching states of switch 8b from the monitor operating, first state to the second or pause state. The timer runs for a short period to allow for stabilization, and at point $T_3$, for example, the zero point may be recalibrated in the above described manner. Particularly, the calibration reflector and the adapting filter drop into the optical path that is closed off in parts by the shutters 8c. The graph will plot a definite zero line. Please note that the zero line as continued to the left of point $t_3$ is the result of instrument turn-off. The instrument is reactivated at point $T_3$ and remains so.

At the point in time $T_4$ the timer in instrument 8 automatically places another particular calibration filter into the light path. The filter may, for example, be representative of 50% light absorbance. No further procedure is necessary because the plotter will write a trace at a particular level which establishes the 50% or 0.5 mark in the graph, to be used, e.g., during subsequent evaluation of the graph. The filter may stay in the path until time $T_5$ when it is removed, and zero calibrating or nulling conditions are restored and maintained during the now ensuing waiting phase to be terminated by stronger dust development. It should be noted that the calibration itself is not a part of the invention, and can follow conventional procedure. It is important that the calibration be timed so as to occur during a phase of negligible dust development.

Just prior or at time $T_6$, blowing of the converter is resumed, and another measuring cycle begins, followed by another calibration step, etc. Thus, unlike the prior art devices, there is a direct functional and time relation between the calibration or recalibration and the dust producing process. In the example given, dust production results directly from the operation of a converter in the blowing mode or phase, indirectly dust is produced by the operation of blower or fan 3 sucking smoke etc. from its point of origin. Conceivably, the photometer could be turned back to its operating mode right after the time $T_5$, but in this specific example of employing the invention, it is advisable to keep shutters 8c closed simply to avoid unnecessary accumulation of dust. At some point in time between $T_5$ and $T_6$, the system may be purged or flushed so as to prevent accumulation of particles that may lodge during each measuring cycle. On the other hand, the invention avoids carrying out of any calibrating procedure during measuring runs proper.

The dust producing phases and the phases of no or little dust production, can be sense otherwise. For example, switching signals (equivalent to those furnished by switch 8b) could be derived from the fan motor 2 or its control circuit. As stated, the motor 2 may not necessarily be always turned off completely but may alternate between high and slow blower speeds.

It is conceivable that for reasons of safety, etc., blower 2 runs always at full speed, particularly if the dust production may continue for other reasons. In this case, the switching signal for operating the devices 8 and 8c could be derived from the plotter. As it drops to near zero, the calibration procedure may be instituted.

The invention is not limited to the embodiments described above but all changes and modifications thereof not constituting departures from the spirit and scope of the invention are intended to be included.

We claim:

1. Method of calibrating and recalibrating a photometric measuring instrument supervising the presence of dust in a particular location and as produced by a process during which dust is developed on an irregular basis, comprising the steps of:
   detecting in the process particular phases during which the dust development is relatively low and the concentration of dust particles in the vicinity of said location is expected to be relatively low as compared with phases of the process other than said particular phases;
   calibrating the instrument as to at least two measuring points in response to said detecting step and during said particular phases following which the supervising of the dust concentration in the particular location is resumed.

2. Method as in claim 1, wherein the dust is developed during blowing of a converter in a steel-making process, the detector responding to termination of the blowing phases as the dust concentration will be low after each blowing phase and prior to the next blowing phase.

3. Method as in claim 1, wherein the process includes intermittent operation of a fan for moving dust-laden air, the detecting step comprising, detecting a change in the operation of the fan on account of the intermittency.

4. Method as in claim 1, wherein the process includes passage of smoke in a flue, the detecting step comprising, detecting the absence or presence of gas flow in the flue, the absence of such flow being indicative of a phase in which dust concentration is expected to be low.

5. Apparatus for determining the calibration of a photometric measuring instrument, supervising the presence of dust in a particular location and as produced by a process during which dust is developed on an irregular basis, comprising:
   means for detecting in the process particular phases during which the dust development is relatively low so that the expected dust concentration in the particular location is expected to be low as compared with other phases of the process; and
   means for timing the calibration of the instrument in response to the detecting as provided by the means for detecting.

6. Apparatus as in claim 5, wherein the means for detecting includes means responsive to production of a flow of a dust containing gas.

* * * * *